US008936616B2

(12) United States Patent
Nelson

(10) Patent No.: US 8,936,616 B2
(45) Date of Patent: Jan. 20, 2015

(54) EXPANDABLE PLUGS AND RELATED DELIVERY APPARATUSES AND METHODS

(75) Inventor: Christopher M. Nelson, Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 544 days.

(21) Appl. No.: 12/796,070

(22) Filed: Jun. 8, 2010

(65) Prior Publication Data
US 2010/0249830 A1 Sep. 30, 2010

Related U.S. Application Data

(63) Continuation of application No. PCT/US2008/084883, filed on Nov. 26, 2008.

(60) Provisional application No. 60/991,343, filed on Nov. 30, 2007.

(51) Int. Cl.
*A61B 17/08* (2006.01)
*A61B 17/00* (2006.01)
*A61B 17/12* (2006.01)
*A61F 6/22* (2006.01)

(52) U.S. Cl.
CPC ........ *A61B 17/0057* (2013.01); *A61B 17/12022* (2013.01); *A61B 17/12109* (2013.01); *A61B 17/12159* (2013.01); *A61B 17/12181* (2013.01); *A61B 17/1219* (2013.01); *A61F 6/22* (2013.01); *A61B 2017/00004* (2013.01); *A61B 2017/00641* (2013.01); *A61B 2017/00654* (2013.01); *A61B 2017/1205* (2013.01)
USPC ........................................................ 606/213

(58) Field of Classification Search
CPC ................ A61B 17/0057; A61B 2017/0057; A61B 2017/00575; A61B 2017/00601; A61B 2017/00619; A61B 2017/00623; A61B 2017/00632; A61B 2017/00898; A61B 2017/00884
USPC ................ 606/157, 191, 194, 198, 213, 232, 606/246–249, 313; 623/17.11–17.16, 623/23.48, 23.46
See application file for complete search history.

(56) References Cited

U.S. PATENT DOCUMENTS

| 4,447,915 | A | * | 5/1984 | Weber .............................. 606/95 |
| 5,522,894 | A | * | 6/1996 | Draenert .................... 623/23.61 |
| 6,251,141 | B1 | * | 6/2001 | Pierson et al. ............. 623/23.48 |
| 2007/0179507 | A1 | | 8/2007 | Shah |
| 2009/0306586 | A1 | * | 12/2009 | Ross et al. ................. 604/93.01 |

FOREIGN PATENT DOCUMENTS

| WO | WO 97/45068 | 12/1997 |
| WO | WO 2006/078578 | 7/2006 |
| WO | WO 2007/002260 | 1/2007 |

* cited by examiner

*Primary Examiner* — Thomas McEvoy
(74) *Attorney, Agent, or Firm* — Woodard, Emhardt, Moriarty, McNett & Henry LLP

(57) ABSTRACT

The present invention provides, in certain aspects, devices and methods for plugging passageways and other open spaces in the body. In one embodiment, a plugging assembly comprises a first plug member and a second plug member, wherein the second plug member is configured to contact and move a portion of the first plug member in plugging a body passageway. These plug members may be formed with one or more of a variety of biocompatible materials including some that are naturally derived and some that are non-naturally derived. In another embodiment, such a plugging assembly is combined with a device that is suitable for delivering the assembly into a body passageway.

27 Claims, 9 Drawing Sheets

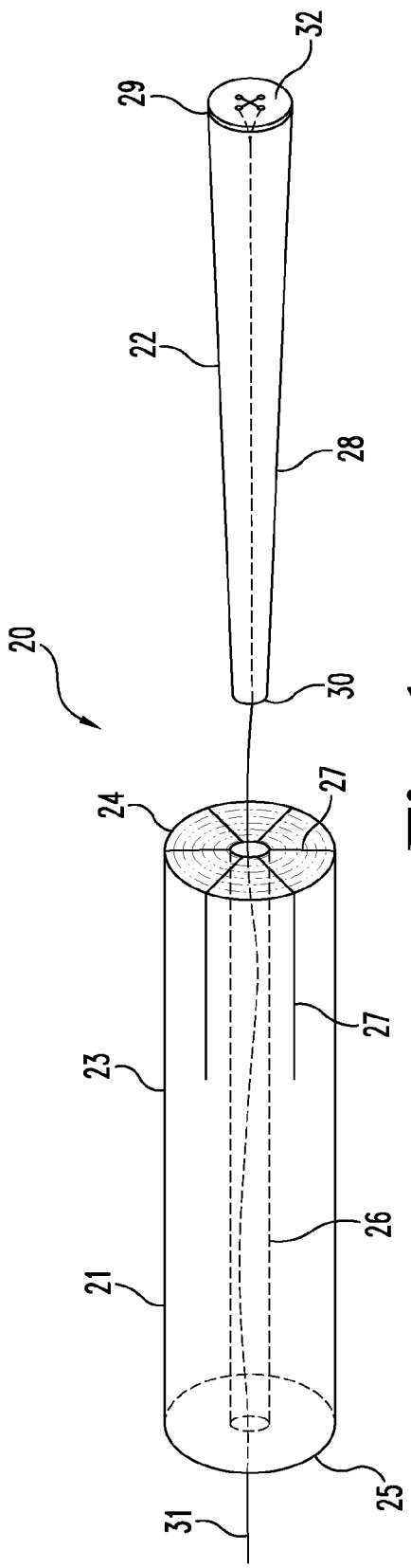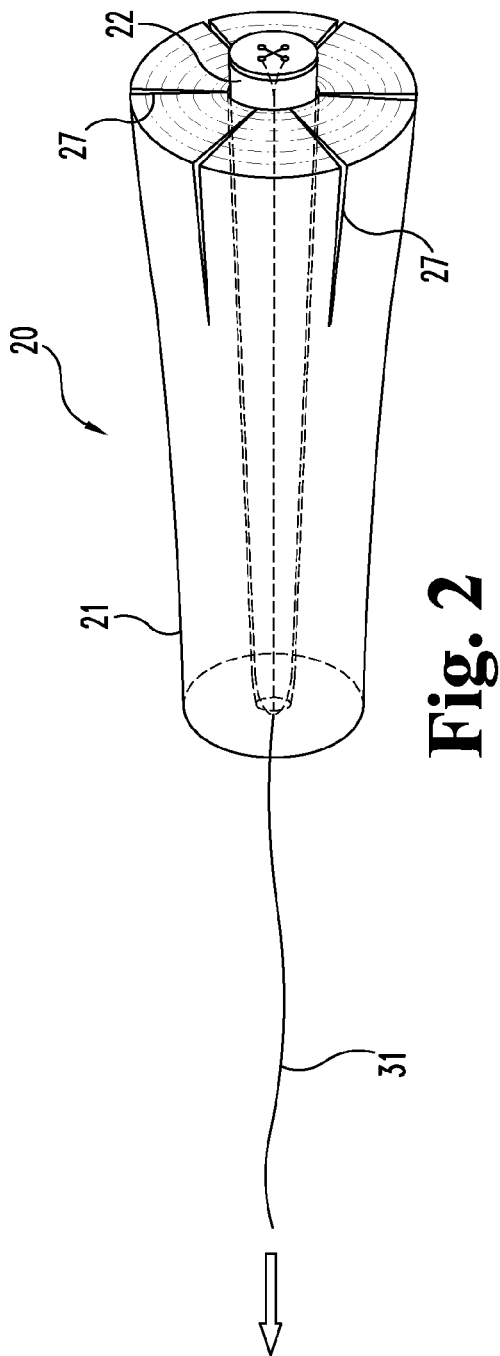

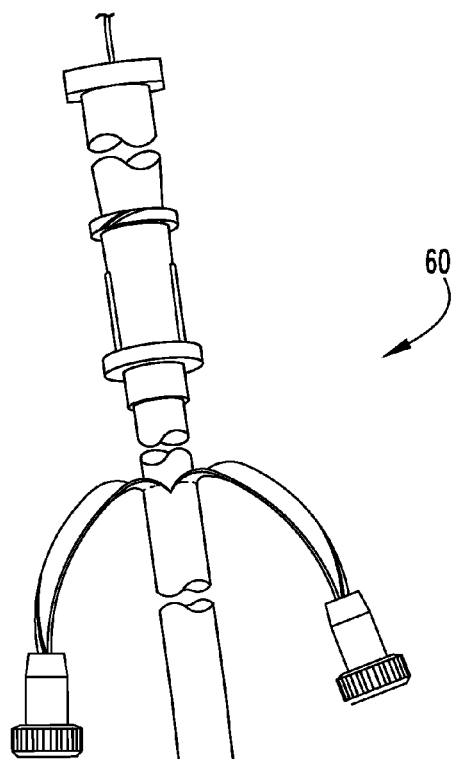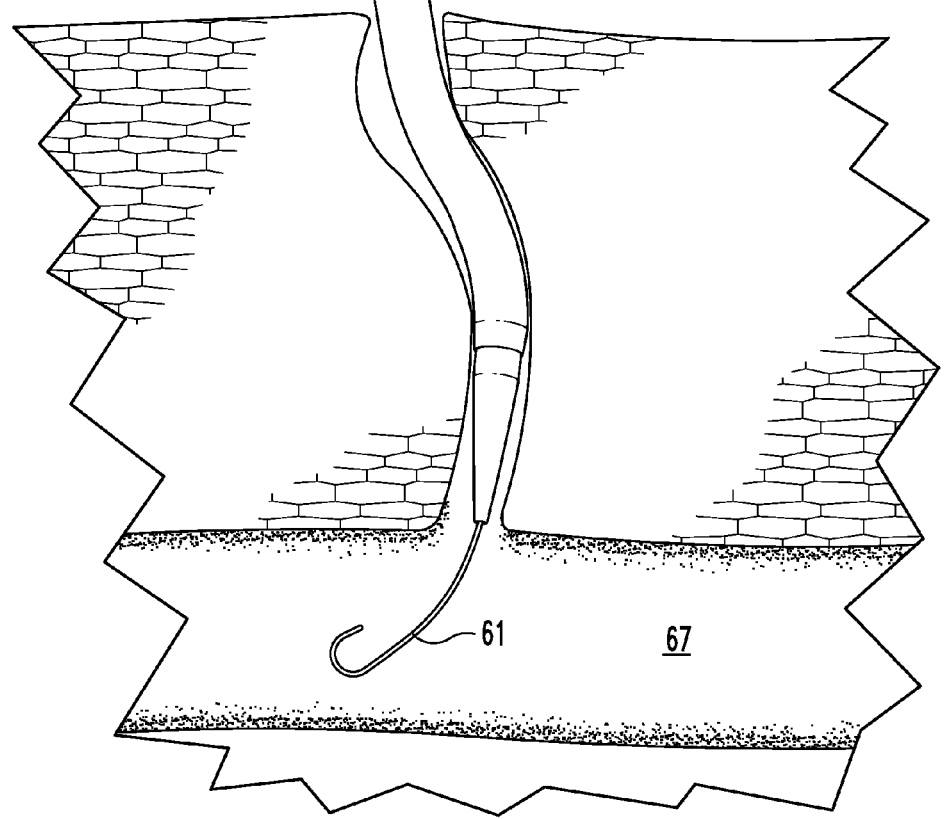
Fig. 5

EXPANDABLE PLUGS AND RELATED DELIVERY APPARATUSES AND METHODS

REFERENCE TO RELATED APPLICATIONS

The present application is a continuation of PCT Patent Application Serial No. PCT/US2008/084883 filed Nov. 26, 2008 entitled " EXPANDABLE PLUGS AND RELATED DELIVERY APPARATUSES AND METHODS" which was published in English under Article 21(2) and which claims the benefit of U.S. Provisional Patent Application Ser. No. 60/991,343, filed Nov. 30, 2007, entitled "EXPANDABLE PLUGS AND RELATED DELIVERY APPARATUSES AND METHODS" both of which are hereby incorporated by reference in their entirety.

BACKGROUND

The present invention relates generally to medical devices and in particular aspects to devices and methods for plugging fistulae and other passageways in the body.

As further background, there exist a variety of passages and other open spaces in the body which can be plugged or otherwise filled to provide benefit to the patient. For example, it may be desirable to occlude a lumen or other open space in the vasculature (e.g., a blood vessel such as a vein or artery). In some instances, a device is deployed within the venous system, e.g., within the greater and/or lesser saphenous vein, to treat complications, such as a varicose vein conditions.

As well, it may be desirable to plug or otherwise fill a fistula. A variety of fistulae can occur in humans. These fistulae can occur for a variety of reasons, such as but not limited to, as a congenital defect, as a result of inflammatory bowel disease, such as Chron's disease, irradiation, trauma, such as childbirth, or as a side effect from a surgical procedure. Further, several different types of fistulae can occur, for example, urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae.

The path which fistulae take, and their complexity, can vary. A fistula may take a take a "straight line" path from a primary opening to a secondary opening, known as a simple fistula. Alternatively, a fistula may comprise multiple tracts ramifying from a primary opening and have multiple secondary openings. This is known as a complex fistula.

Anorectal fistulae can result from infection in the anal glands, which are located around the circumference of the distal anal canal that forms the anatomic landmark known as the dentate line. Approximately 20-40 such glands are found in humans. Infection in an anal gland can result in an abscess. This abscess then can track through soft tissues (e.g., through or around the sphincter muscles) into the perianal skin, where it drains either spontaneously or surgically. The resulting void through soft tissue is known as a fistula. The internal or inner opening of the fistula, usually located at or near the dentate line, is known as the primary opening. Any external or outer openings, which are usually located in the perianal skin, are known as secondary openings.

One technique for treating a perianal fistula is to make an incision adjacent the anus until the incision contacts the fistula and then excise the fistula from the anal tissue. This surgical procedure tends to sever the fibers of the anal sphincter, and may cause incontinence. Other surgical treatment of fistulae involve passing a fistula probe through the tract of the fistula in a blind manner, using primarily only tactile sensation and experience to guide to probe. Having passed the probe through the fistula tract, the overlying tissue is surgically divided. This is known as a fistulotomy. Since a variable amount of sphincter muscle is divided during the procedure, fistulotomy also may result in impaired sphincter control, and even frank incontinence.

A gastrointestinal fistula is an abnormal passage that leaks contents of the stomach or the intestine (small or large bowel) to other organs, usually other parts of the intestine or the skin. For example, gastrojejunocolic fistulae include both enterocutaneous fistulae (those occurring between the skin surface and the intestine, namely the duodenum, the jejunum, and the ileum) and gastric fistulae (those occurring between the stomach and skin surface). Another type of fistula occurring in the gastrointestinal tract is an enteroenteral fistula, which refers to a fistula occurring between two parts of the intestine. Gastrointestinal fistulae can result in malnutrition and dehydration depending on their location in the gastrointestinal tract. They can also be a source of skin problems and infection. The majority of these types of fistulae are the result of surgery (e.g., bowel surgery), although sometimes they can develop spontaneously or from trauma, especially penetrating traumas such as stab wounds or gunshot wounds. Inflammatory processes, such as infection or inflammatory bowel disease (Crohn's disease), may also cause gastrointestinal fistulae. In fact, Crohn's disease is the most common primary bowel disease leading to enterocutaneous fistulae, and surgical treatment may be difficult because additional enterocutaneous fistulae develop in many of these patients postoperatively.

Treatment options for gastrointestinal fistulae vary. Depending on the clinical situation, patients may require IV nutrition and a period of time without food to allow the fistula time to close on its own. Indeed, nonsurgical therapy may allow spontaneous closure of the fistula, although this can be expected less than 30% of the time according to one estimate. A variable amount of time to allow spontaneous closure of fistulae has been recommended, ranging from 30 days to 6 to 8 weeks. During this preoperative preparation, external control of the fistula drainage prevents skin disruption and provides guidelines for fluid and electrolyte replacement. In some cases, surgery is necessary to remove the segment of intestine involved in a non-healing fistula.

When surgery is deemed necessary, one operation for fistula closure is resection of the fistula-bearing segment and primary end-to-end anastamosis. The anastomosis may be reinforced by greater omentum or a serosal patch from adjacent small bowel. Still other methods for treating fistulae involve injecting sclerosant or sealant (e.g., collagen or fibrin glue) into the tract of the fistula to block the fistula. Closure of a fistula using a sealant is typically performed as a two-stage procedure, including a first-stage seton placement and injection of the fibrin glue several weeks later. This allows residual infection to resolve and to allow the fistula tract to "mature" prior to injecting a sealant. If sealant or sclerosant were injected as a one-stage procedure, into an "unprepared" or infected fistula, this may cause a flare-up of the infection and even further abscess formation.

There remain needs for improved and/or alternative devices, systems and methods for plugging passageways and other open spaces in the body. The present invention is addressed to those needs.

SUMMARY

The present invention provides, in certain aspects, unique devices for insertion into passageways or other similar openings in the body. Such devices in some embodiments include a first element cooperable with a second element to provide an implanted configuration to be received at the targeted insertion site. The cooperation between the two elements can be in a controlled fashion; e.g. wherein portions of the first and second elements engage and potentially translate along one another in a fashion that is predictably controlled by engaged surface features of the first and second elements. Some of these devices have a portion that is outwardly displaced when contacted by another device component. In one embodiment, a device comprises a first plug member and a removable second plug member positioned in the first plug member. When so positioned, the second plug member is effective to radially expand at least a segment of the first plug member. This device can exhibit any suitable size, shape and configuration for plugging a passageway in the body, and be may be formed with one or more of a variety of biocompatible materials including some that are naturally derived and some that are non-naturally derived. In a preferred embodiment, the first plug member and/or the second plug member is comprised of a remodelable, angiogenic material, for example, a remodelable extracellular matrix material such as submucosa.

In another aspect, the invention provides an assembly for plugging a passageway in the body that includes a first plug member and a second plug member. The second plug member is positionable in the first plug member, and in the first plug member, is effective to outwardly displace at least part of the first plug member. Each of these plug members can exhibit a variety of shapes and sizes, and the second plug member can be positioned at any suitable location in the first plug member for plugging the body passageway. Although not necessary to broader aspects of the invention, in one form, the first plug member provides a designated opening (e.g., a lumen or other passage) into which the second plug member can be positioned.

An additional embodiment of the invention provides a method for plugging a passageway in the body, which utilizes a plugging assembly including a first plug member and a second plug member. In one step, the first plug member and the second plug member are delivered to the body passageway. Thereafter, relative movement between the first plug member and the second plug member is brought about, wherein contact between the first plug member and the second plug member outwardly displaces at least part of the first plug member for plugging the body passageway. In some instances, such contact causes the circumference of the first plug member, or a portion thereof, to increase. Causing relative movement between the first plug member and the second plug member can be achieved in a variety of manners including some that involve pushing and/or pulling one or both plug members in the body passageway. In one aspect, a lumen extends through the first plug member, and a pulling device, which can be attached to or otherwise associated with the second plug member, is passed through this lumen. This pulling device (e.g., an attached suture or a grasping instrument) can then be used in positioning the second plug member in this first plug member lumen.

Another aspect of the invention provides an apparatus for plugging a passageway in the body. This apparatus includes a delivery device that has a lumen communicating with a distal end opening, and is configured for passage through a body passageway. The apparatus also includes a first plug member and a second plug member, both received in the delivery device lumen. The second plug member is positionable in the first plug member, and in the first plug member, is effective to outwardly displace at least part of the first plug member for plugging the body passageway. This delivery device can exhibit any suitable size, shape and configuration for delivering the first plug member and second plug member into the body passageway, and in some embodiments, is flexible to enhance its travel through particular body passageways. In one aspect, the apparatus includes a pusher device, which is translatable through the delivery device lumen, and can be used in expelling the first plug member and/or the second plug member from the distal end opening.

A further embodiment of the invention provides a method for plugging a passageway in the body, which utilizes a plugging apparatus such as that described above. In one step, the delivery device is passed through at least a segment of the body passageway. In other steps, the first plug member and the second plug member are removed from the delivery device lumen. The first plug member is positioned at a location in the body passageway. Thereafter, relative movement between the first plug member and the second plug member is brought about, wherein contact between the first plug member and the second plug member outwardly displaces at least part of the first plug member for plugging the body passageway.

Yet another aspect of the present invention provides a method for plugging a passageway in the body. In this method, a plugging assembly comprising a first plug member and a second plug member is provided. The first plug member, which has a lumen, is delivered to the body passageway. Thereafter, at least part of the first plug member lumen is filled with the second plug member.

In another embodiment, the invention provides an assembly for plugging a passageway in the body. This assembly includes a first plug member and a second plug member. The first plug member has a cavity, and is positionable in a body passageway. The second plug member is comprised of a porous, collagen-containing matrix material, and includes a segment positionable in the cavity of the first plug member. Additionally, the second plug member has a first condition suitable to deliver the segment to the first plug member cavity, and a second, expanded condition providing a more snug fit of the segment in the first plug member cavity relative to the first condition of the second plug member.

Other objects, embodiments, forms, features, advantages, aspects, and benefits of the present invention shall become apparent from the detailed description and drawings included herein.

BRIEF DESCRIPTION OF THE DRAWINGS

FIG. 1 is a perspective view of an inventive assembly including a first plug member and a second plug member.

FIG. 2 shows the assembly of FIG. 1 with the first plug member positioned in the second plug member.

FIG. 5 shows the apparatus of FIG. 4 at a different stage of delivery.

DETAILED DESCRIPTION

Figure 3:
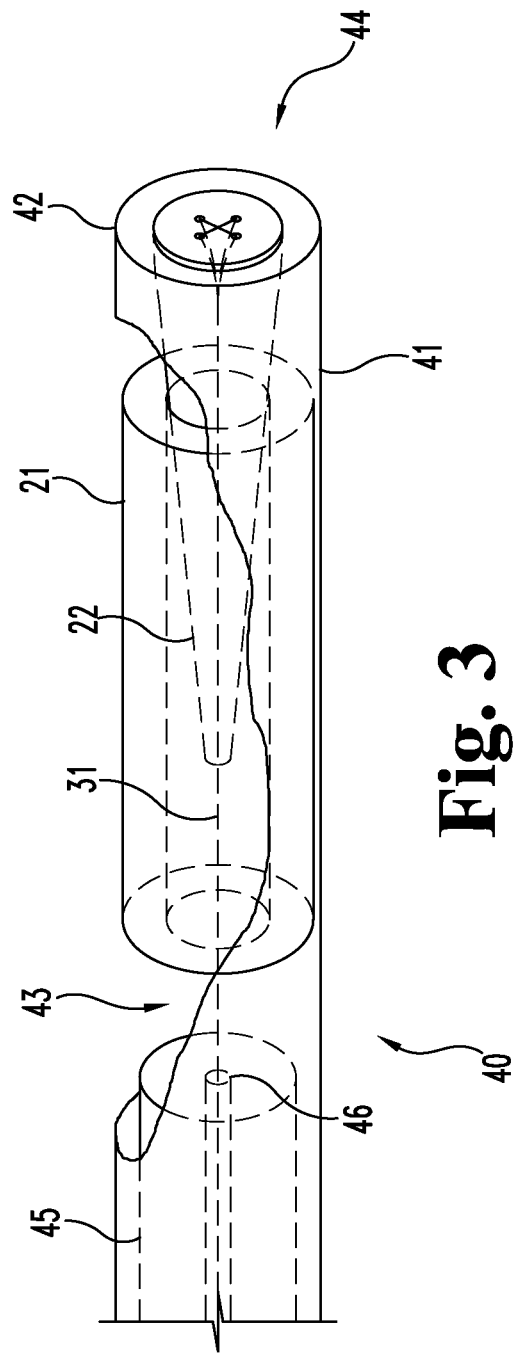
FIG. 3 shows the assembly of FIG. 1 received in a delivery device lumen.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique assemblies for plugging passageways in the body. One such assembly comprises a first plug member and a second plug member, wherein the second plug member is positionable in the first plug member to expand at least a segment of the first plug member to plug a body passageway. In one embodiment, an assembly of this sort is combined with a device that is suitable for delivering the assembly into a body passageway. An illustrative delivery device has a lumen communicating with a distal end opening, wherein the first plug member and the second plug member can be received in the delivery device lumen for removal from the distal end opening in the body. The present invention also provides methods for plugging passageways in the body. One such method utilizes an assembly such as that described above. In one step, a first plug member is positioned at least partially in the body passageway, and in another step, a second plug member is positioned in the first plug member, wherein at least a segment of the first plug member expands (e.g., radially expands) to plug the body passageway.

Assemblies and devices of the invention may be used to plug or otherwise fill a variety of passages or other open spaces in the body. In some instances, these open spaces will occur naturally in the body, for example, as a native lumen or other open space in a bodily system, e.g., in an organ or other component of the circulatory, respiratory, digestive, urinary and reproductive, sensory, or endocrine systems. In certain aspects, a space to be filled is one that exists naturally in the body but relates to a disease, defect, deformation, etc. Alternatively, an opening or passage to be filled may be one resulting from an intentional or unintentional trauma to the body including but not limited to some relating to vehicular accidents, gunshots and other similar wounds, etc., as well as some formed by passage of a medical instrument (e.g., a needle, trocar, etc.) through cutaneous, subcutaneous, and/or intracutaneous tissue.

Illustratively, inventive devices and assemblies, alone or in conjunction with one or more other suitable objects, can be used to occlude, or at least promote and/or facilitate occlusion of, a lumen or other open space in the vasculature, e.g., a blood vessel such as a vein or artery, or a lumen or open space of a fallopian tube, e.g. in a procedure to provide sterility to a female patient. In certain aspects, one or more assemblies of the invention are deployed within the venous system (e.g., within the greater and/or lesser saphenous vein) to treat complications, such as a varicose vein conditions. In other embodiments, inventive assemblies are used as contraceptive devices. In preferred embodiments, assemblies of the invention can be used to plug or otherwise fill fistulae such as but not limited to urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae.

With reference now to FIG. 1, shown is an assembly 20 which can be used to plug a passageway or other open space in a patient's body. Assembly 20 includes a first plug member 21 and a second plug member 22. First plug member 21 is comprised of an elongate body 23 having a first end 24 and second end 25. Body 23 is generally in the shape of a cylinder, although a variety of other shapes are contemplated as within the scope of the present invention. In general, body 23 will be shaped and sized so that at least a portion of body 23, and in some cases all of body 23, can be positioned in a space to be plugged.

A lumen 26 extends through body 23 from its first end 24 to its second end 25. Although not necessary to broader aspects of the invention, such a plug member lumen can provide a channel into which a second plug member such as second plug member 22 can be received. When present, a plug member lumen can exhibit a variety of shapes and sizes to suit a particular application, for example, having a constant or varying diameter along its length. In certain embodiments, a plug member lumen may include a tapered longitudinal portion. In general, the dimensions of a plug member lumen, when used to receive one or more other plug members therein, will be selected based on the characteristics of these one or more other plug members and/or other factors such as but not limited to conditions at the treatment site and other characteristics of first plug member 21.

Continuing with FIG. 1, second plug member 22 is comprised of an elongate body 28 having a first end 29 and a second end 30. In general, inventive assemblies such as assembly 20 will include at least one plug member that can be caused or allowed to contact and move a portion of another plug member in providing a plugging arrangement. Illustratively, second plug member 22 can be positioned in first plug member 21, and when so positioned, is effective to outwardly displace portions of first plug member 21. In this specific illustrative embodiment, such displacement provides radial expansion of at least part of the length of the first plug member, for example, a part that includes first end 24 as generally shown in FIG. 2. Body 28 is generally in the shape of a truncated cone, although a variety of other shapes are contemplated as within the scope of the present invention. In this regard, it will be understood that a plug member (e.g., second plug member 22) can exhibit any suitable size and shape to provide the desired movement (e.g., outward displacement) of a portion of another plug member (e.g., first plug member 21) in which it is positioned. Second end 30 of second plug member 22 provides a leading or guiding portion for controlling orientation of contact with first plug member 21.

Second plug member 22 has at least a segment that increases in circumference moving from its second end 30 toward its first end 29, while lumen 26 has a generally constant circumference along its length. Second end 30 has roughly the same circumference as (or a slightly smaller circumference than) lumen 26, and first end 29 has a somewhat larger circumference than lumen 26. In this regard, as the second end 30 of second plug member 22 is advanced through lumen 26 from first end 24 toward second end 25, portions of second plug member having a larger circumference than lumen 26 (e.g., portions including first end 29) exert pressure on the wall defining lumen 26. This pressure causes portions of first plug member 21 to move in an outward direction, which in turn, increases the circumference of at least a portion of first plug member 21. As described more thoroughly below, one or more cuts or other adaptations for promoting and/or facilitating such movement can be incorporated into elongate body 23. In an alternative embodiment, the second plug member has a generally constant diameter along its length, and the first plug member lumen is tapered such that a desired displacement is achieved when the second plug member is advanced through the lumen from the larger-diameter end toward the smaller-diameter end. In some forms, a plug member having a tapered portion is positioned in a plug member lumen having a tapered portion.

In addition what is shown in FIG. 1, the invention provides a variety of other plug body configurations such as that of second plug member 22, wherein a plug body occupies an increased volume moving along at least part of the plug body, for example, having a gradually increasing volume moving from one end of the plug body to the other. Illustratively, a plug member that is to be positioned in a lumen of another plug member can include a biocompatible sheet-form material, wherein one longitudinal portion of the sheet occupies an increased volume (e.g., is relatively wider and/or thicker) than another longitudinal portion of the sheet (of a similar length). In such forms, at least a portion of the sheet will be deformable upon impingement by the plug lumen wall, and will be sized and shaped so as to be deformable to a three-dimensional volumetric body filling at least a portion of the plug lumen. In this regard, as a portion of the sheet is drawn into the lumen, it can fold and/or roll over itself one or more times to conform to the lumen wall and gradually become "wedged" into the lumen when sufficiently pulled therethrough. In some instances, such positioning will exert pressure on the wall defining the lumen, causing at least a portion of that plug member to become outwardly displaced. Also, such wedging or lodging may be sufficient to obviate the need for otherwise securing the sheet to the other plug member and/or soft tissues at the treatment site, although additional steps to secure the sheet in place (e.g., suturing to the other plug member) may be taken.

In one aspect, a plug member to be positioned in another plug member comprises a compliant, biocompatible sheet-form material, for example, one or more layers of ECM material that can be pulled into a plug member lumen. Such sheet-form plug members can be prepared, for example, as described in International Patent Application Serial No. PCT/US2006/16233, filed Apr. 29, 2006, and entitled "FISTULA GRAFT WITH DEFORMABLE SHEET-FORM MATERIAL" (Cook Biotech Incorporated), which is hereby incorporated by reference in its entirety.

A plugging assembly of the invention, or any component thereof, may be formed with one or more of a variety of biocompatible materials including some that are naturally derived and some that are non-naturally derived. In the specific illustrative embodiment depicted in FIG. 1, body 23 is formed with layers of sheet-form ECM material that are compressed and bonded together (e.g., around a mandrel) so as to form a substantially unitary, rolled construct. In other embodiments, body 23 is formed with sheet-form material configured differently than what is shown in FIG. 1 (e.g., different number of layers, different layer thickness, differently rolled or otherwise assembled, etc.), or is formed with a non-sheet-form material as described elsewhere herein. Body 28 is similarly formed with layers of sheet-form ECM material that are compressed and bonded together so as to form a substantially unitary, rolled construct.

In certain aspects, a first plug member includes one or more adaptations for enhancing expansion of external features of the first plug member when a second plug member is brought into contact with the first plug member. Such adaptations can include one or more perforations, cuts, channels, indentations, scores, etc. in the plug member. These and other adaptations for enhancing the expansive ability of the first plug member will be recognized by the skilled artisan and are encompassed by the present invention. In the current embodiment, a plurality of cuts 27 is formed in elongate body 23. Each cut extends a distance from first end 24 toward second end 25, as well as from an outer surface of body 23 to lumen 26, although additional cut configurations and placements in the plug member body are contemplated as within the scope of the present invention. Illustratively, a cut or other adaptation can extend any suitable distance along a plug member (e.g., can run down the entire length of a plug member), and can extend through a plug member any suitable distance and at any suitable angle.

In the current embodiment, positioning second plug member 22 in first plug member 21 forces parts of first plug member 21 outward, causing the circumference of at least a portion of first plug member 21 to increase. In other embodiments, positioning a second plug member in a first plug member also forces parts of the first plug member outward; however, the circumference of the first plug member increases very little or not at all. Rather, these parts of the first plug member are compressed as they are forced outward, which in turn, increases the densities of these parts. Additionally or alternatively, positioning a second plug member in a first plug member can, in some aspects of the invention, compress and increase the density of a portion of the second plug member, for example, with little or no outward movement of the first plug member. Such relatively higher density plug portions may be beneficial in a variety of plugging operations. For example, having material with a relatively more dense structure at or near a primary fistula opening can inhibit bacteria and other undesirable substances from passing from the alimentary canal and into the fistula.

Referring again to FIG. 1, a pulling device in the form of a resorbable suture 31 extends a distance from the second end 30 of second plug member 22. This suture can extend any suitable distance from the second plug member, and in some cases, will extend from about 1 cm to about 100 cm, more typically from about 20 cm to about 80 cm, and even more typically from about 40 cm to about 80 cm from its smaller end. As shown, suture 31 can extend through first plug member lumen 26, and in this regard, is effective for pulling second plug member 22 into first plug member 21. Second plug member 22 also includes an end cap 32 at its first end 29. End cap 32 may or may not be attached to first end 29. In the current illustrated embodiment, suture 31 passes through and around end cap 32, and extends through second plug member 22 along its length. In certain embodiments, suture 31 is attached to the material of second plug member 22, e.g. by being securely embedded therein or knotted thereto.

In accordance with the present invention, a plug member can be positioned in contact with another plug member in any suitable manner including some that involve directly or indirectly pushing and/or pulling one or both plug members in the body. As well, such positioning can be performed directly by hand in situations where such access is possible, although in some embodiments, positioning one plug member in another plug member will additionally or alternatively involve the use of one or more instruments. In one aspect, a lumen extends through a first plug member, and a pulling device, which is attached to or otherwise associated with a second plug member, is passed through this lumen. The pulling device can then be used in positioning the second plug member in this first plug member lumen.

For example and referring again to FIGS. 1 and 2, suture 31 or another elongate flexible tether can be used to pull the second end 30 of second plug member 22 into lumen 26 at the first end 24 of first plug member 21. Thereafter, second plug member 22 can be advanced through lumen 26 in the direction of the arrow, i.e., toward the second end 25 of first plug member 21, until second plug member 22 is desirably seated in first plug member 21. Second plug member 22 may be positioned so that its first end 29 extends a distance from the first end 24 of first plug member 21 as shown in FIG. 2, or alternatively, second plug member first end 29 may be pulled flush with first plug member first end 24 or a distance into lumen 26. In an alternative embodiment, a probe or other suitable instrument (e.g., a suitably configured pair of surgical hemostats) includes a portion that is passable through the lumen of a first plug member, and can be used to pull a second plug member into this lumen, either by directly contacting the second plug member or by contacting an associated suture, etc. Such an instrument in certain forms can include a gripping portion for securing the second plug member or suture. As will be understood by those skilled in the art, the second end 30 of second plug member 22 could also be pushed into lumen 26 at the first end 24 of first plug member 21 using an appropriate instrument or technique.

In certain embodiments, a plugging assembly includes a radiopaque element. For example, an assembly component such as end cap 32 can be comprised of a radiopaque substance or device such as but not limited to a radiopaque coating, attached radiopaque object, or integrated radiopaque substance useful for determining the location of the component in the body. In certain forms, cap 32 can be formed of a polymeric material loaded with a particulate radiopaque material. In this regard, any suitable radiopaque substance, including but not limited to, tantalum such as tantalum powder, can be incorporated into an inventive component. Other radiopaque markers may be comprised of gold, bismuth, iodine, and barium, as well as other suitable radiopaque materials.

Turning now to a more detailed discussion of materials useful in forming plug members of the invention, these materials should generally be biocompatible, and in advantageous embodiments of the assemblies, are comprised of a remodelable material. Particular advantage can be provided by plug members including a remodelable collagenous material. Such remodelable collagenous materials, whether reconstituted or naturally-derived, can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth on, around, and/or within tissue in which an plugging device of the invention is implanted, e.g., around tissue defining a fistula tract, an opening to a fistula, or another space in the body.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Submucosa-containing or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Plug members of the invention can include xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

ECM materials used in the invention may be essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

Turning now to a discussion of drying techniques that can be useful in certain embodiments of the invention, drying by evaporation, or air drying, generally comprises drying a partially or completely hydrated remodelable material by allowing the hydrant to evaporate from the material. Evaporative cooling can be enhanced in a number of ways, such as by placing the material in a vacuum, by blowing air over the material, by increasing the temperature of the material, by applying a blotting material during evaporation, or by any other suitable means or any suitable combination thereof. The amount of void space or open matrix structure within an ECM material that has been dried by evaporation is typically more diminished than, for example, an ECM material dried by lyophilization as described below.

A suitable lyophilization process can include providing an ECM material that contains a sufficient amount of hydrant such that the voids in the material matrix are filled with the hydrant. The hydrant can comprise any suitable hydrant known in the art, such as purified water or sterile saline, or any suitable combination thereof. Illustratively, the hydrated material can be placed in a freezer until the material and hydrant are substantially in a frozen or solid state. Thereafter, the frozen material and hydrant can be placed in a vacuum chamber and a vacuum initiated. Once at a sufficient vacuum, as is known in the art, the frozen hydrant will sublime from the material, thereby resulting in a dry remodelable material.

In alternative embodiments, a hydrated ECM material can be lyophilized without a separately performed pre-freezing step. In these embodiments, a strong vacuum can be applied to the hydrated material to result in rapid evaporative cooling which freezes the hydrant within the ECM material. Thereafter, the frozen hydrant can sublime from the material thereby drying the ECM material. Desirably, an ECM material that is dried via lyophilization maintains a substantial amount of the void space, or open matrix structure, that is characteristic of the harvested ECM material.

Drying by vacuum pressing generally comprises compressing a fully or partially hydrated remodelable material while the material is subject to a vacuum. One suitable method of vacuum pressing comprises placing a remodelable material in a vacuum chamber having collapsible walls. As the vacuum is established, the walls collapse onto and compress the material until it is dry. Similar to evaporative drying, when a remodelable material is dried in a vacuum press, more of the material's open matrix structure is diminished or reduced than if the material was dried by lyophilization.

In certain aspects, the invention provides plugging assemblies, devices, etc. that include a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents such as those described above. A combination of one or more of these with dehydration-induced bonding may also be used to bond ECM material layers to one another.

A variety of dehydration-induced bonding methods can be used to fuse together portions of an ECM material. In one preferred embodiment, multiple layers of ECM material are compressed under dehydrating conditions. In this context, the term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressed surfaces. One particularly useful method of dehydration bonding ECM materials is lyophilization.

Another method of dehydration bonding comprises pulling a vacuum on the assembly while simultaneously employing the vacuum to press the assembly together. Again, this method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying and other operations under relatively mild temperature exposure conditions that minimize deleterious effects upon any ECM materials being used, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

As well, plugging assemblies of the invention may be comprised of biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Plugging assemblies of the invention can also include a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

A plugging assembly and any of its components may be sized and configured in a number of manners for use in accordance with the present invention. In some forms, a plug member is comprised of an elongate plug body, either having a constant or varying cross-sectional area along its length. For example, elongate plug bodies useful in the invention may exhibit a generally cylindrical shape, a conical shape, a shape having tapered and non-tapered longitudinal portions, or other suitable shapes having rectilinear and/or curvilinear portions.

In embodiments where an inventive assembly is used to treat a fistula, such an assembly will generally be configured to extend through a fistula tract (or a segment thereof), and in some cases, will be sufficient to plug or otherwise fill at least a segment of the tract. In certain embodiments, an assembly will have a length of at least about 0.20 cm, and in many instances at least about 1 cm to about 20 cm (approximately 1 to 8 inches) for plugging a fistula tract. In some cases, an assembly will have a length of from about 2 cm to about 5 cm, or alternatively, from about 2 inches to about 4 inches. Additionally, an assembly useful in the invention, or any portion thereof, can have a diameter, which may or may not be constant along its length, from about 0.1 mm to about 25 mm, or more typically from about 5 mm to about 15 mm. In certain forms, a generally conical assembly is tapered along its length so that one end of the assembly has a diameter of about 5 mm to about 15 mm, while the opposite end of the assembly has a diameter of about 0.5 mm to about 5 mm. Such a taper may or may not be continuous along the length of the assembly.

The plug members described herein can be formed in any suitable manner including but not limited to by extrusion, using a mold or form, construction around a mandrel, and/or combinations or variations thereof. In some embodiments, a plug member is formed with a reconstituted or otherwise reassembled ECM material. Plug members can also be formed by folding or rolling, or otherwise overlaying one or more portions of a biocompatible material, such as a biocompatible sheet material. The overlaid biocompatible sheet material can be compressed and dried or otherwise bonded into a volumetric shape such that a substantially unitary construct is formed. In some forms, an inventive assembly component is constructed by randomly or regularly packing one or more pieces of single or multilayer ECM sheet material within a mold and thereafter processing the packed material. Plug member bodies useful in the invention can be prepared, for example, as described in International Patent Application Serial No. PCT/US2006/16748, filed Apr. 29, 2006, and entitled "VOLUMETRIC GRAFTS FOR TREATMENT OF FISTULAE AND RELATED METHODS AND SYSTEMS" (Cook Biotech Incorporated), which is hereby incorporated by reference in its entirety.

Methods for forming assembly components useful in the invention can involve manipulating a material within a mold or form. It should be noted that this material may or may not be hydrated when placed in, on, around, etc. the mold or form. In some methods, a substantially dry ECM material (e.g., a powder or sheet material) can be placed in a mold and then suitably hydrated for further processing. In other methods, a hydrated starting material is placed in and/or on a mold or forming structure for further processing. For example, one or more hydrated sheets of ECM material can be applied to a form, e.g., wrapped at least partially around a mandrel so that portions of the sheet(s) overlap. Then, the one or more sheets can be dried, and in some embodiments, dried while under compression, to form a unitary graft construct.

In some modes of operation, a hydrated graft material is provided within a single- or multiple-part mold having a plurality of apertures or holes extending through a wall of the mold, thereby providing access to the mold interior from an external location. These apertures can serve to enhance drying of a hydrated material during a processing step and in processes exerting vacuum pressure at these apertures, can promote and/or facilitate formation of surface protuberances on the graft material as portions of the same are drawn toward the apertures while under vacuum. In one aspect, an amount of ECM material is retained in such a mold, and needles or other material-displacing objects are inserted through some or all of the mold apertures and a distance into the ECM material, thereby displacing volumes of the ECM material. This can be performed when the graft material is hydrated, partially hydrated or dehydrated. In some forms, with needles inserted in a hydrated ECM material and providing passages therein, the material is subjected to conditions (e.g., freezing and/or dehydrating conditions) which, alone or in combination with one or more other conditions, cause or allow the passages to be generally retained in the ECM material after the needles are removed.

In one embodiment, one or more sheets of hydrated ECM material are suitably wrapped and/or randomly packed around a mandrel, and then a mold having a plurality of holes extending through a wall of the mold is placed around the material-covered mandrel, for example, so that an amount of pressure is placed on the ECM material. The mandrel can then optionally be removed. Thereafter, needles or other material-displacing objects are inserted through some or all of the holes and at least partially through the ECM material, thereby displacing volumes of the ECM material. The ECM material is then at least partially dried. In some aspects, a suitable lyophilization technique is employed, e.g., one with or without a pre-freezing step as described herein. In these or other drying methods in which needles or other penetrating elements are to be left within the mass during drying, these elements can optionally be provided with a plurality of apertures or holes or can otherwise be sufficiently porous to facilitate the drying operation by allowing the passage of hydrate from the wet mass. In one embodiment, a hydrated ECM material with emplaced needles can be subjected to freezing conditions so that the material and any contained hydrate become substantially frozen. Thereafter, the needles can be removed from the ECM material, and the remaining construct (with the frozen material passages substantially retaining their shape) can be placed under a vacuum so that the frozen hydrant sublimes from the material, thereby resulting in a dry graft construct with retained passages therein.

In other modes of operation, passage-forming stuctures can be incorporated integrally into a mold so that passageways are formed upon introducing the starting material in and/or on the mold. In these aspects, the passage-forming structures can be part of the mold (e.g., extend from a surface of the mold), or they can be separate objects attached or otherwise coupled to the mold, to provide the desired passage or passages through the ultimately-formed graft body.

Although not necessary to broader aspects of the invention, in some aspects, the formation of such a graft construct comprises wrapping one or more sheets of hydrated graft material around a mandrel a number of times. The resulting roll of graft material is then introduced into a mold, and the mandrel is removed (optional), e.g., before or after applying the mold. Thereafter, multiple material-displacing objects such as but not limited to needles are forced through apertures in the mold and into the hydrated graft material, and the material is subjected to one or more drying techniques such as a lyophilization process. In other aspects, the formation of such a graft construct includes placing a flowable graft material into a mold and then subjecting the graft material to further processing. For example, a flowable ECM material mass, such as a gel, paste or putty, potentially incorporating a particulate ECM material, can be placed into a mold, and then with volumes of material displaced in the mass (e.g., by penetrating needles), the ECM material can be dried or otherwise caused to form an integral piece to provide a graft body having passages therein. Illustratively, each of the passages can be provided by forcing a single object through the material mass, or alternatively, where a mandrel is left in place to form a longitudinal lumen, by forcing two objects into the mass and toward one another from opposite directions until they abut the mandrel. The mass can then be processed to a solid graft body as discussed herein.

Now turning to a more detailed discussion of devices and methods useful in delivering plugging assemblies of the invention into body passageways, in some embodiments, an inventive assembly, or any component thereof, is delivered into a body passageway or other open space with the aid of a delivery device. Illustratively, a plugging assembly can be deployed using a sheath or catheter configured to enter the body passageway, and can optionally be located within the passageway over a guidewire or under endoscopic guidance. In these embodiments, an assembly can be deployed in an over-the-wire configuration or through an unobstructed delivery device lumen.

Delivery devices useful in certain aspects of the present invention have a lumen communicating with a distal, open end. This "leading" distal end is configured to pass into passageways and other open spaces in the body. Although not necessary to broader aspects of the invention, this distal end, or any portion thereof, may be particularly configured to enhance travel of the device through certain body passageways, for example, including a tapered portion and/or having a dome-shaped or otherwise rounded tip. Accordingly, such devices can exhibit any suitable size, shape and configuration for performing the functions described herein, while avoiding substantially cutting or tearing surrounding soft tissues.

In certain embodiments, a delivery device will be used to deliver an assembly into a fistula tract. Such a device may have a length of about 2 inches to about 12 inches, more typically about 3 inches to about 9 inches, and even more typically about 4 to about 8 inches. Also, these devices may have an outside diameter of about 0.3 mm to about 3.2 mm, more typically about 0.5 to about 3.0 mm, and even more typically about 1.0 mm to about 2.5 mm.

In other embodiments, a delivery device is rigid or substantially rigid, and is configured to be generally straight, for example, for use in treating certain simple or straight fistulae. Alternatively, delivery devices useful in the invention can be configured to include one or more portions that are curvilinear, bent, or otherwise suitably shaped. In certain aspects, the distal end of a delivery device is curved to a degree to allow for easier passage of the distal end through a complex fistula, e.g., a horseshoe fistula, and/or through the primary fistula opening and into the alimentary canal. In some forms, a delivery device is composed of a malleable material such as but not limited to a woven or spirally-configured metal or alloy material, or a plastic (hydrocarbon-based) material, which may be bent to the necessary angle or curvature, for example, to allow passage through a fistula tract. The shape of such a delivery device may be adjusted at certain intervals of the procedure so as to allow the delivery device to pass further and further into the fistula tract, until the primary opening is identified. In some forms, the delivery device is generally straight in a relaxed condition but can flex to adapt to contours during passage.

In this regard, delivery devices, when used in the invention, can be formed with one or more of a variety of materials. A particular material may be selected to take advantage of one or more of its properties such as but not limited to its weight, durability, flexibility, etc. For example, a device may comprise a material having properties that allow the device to traverse a body passageway without buckling or kinking or causing unacceptable damage to soft tissues defining the passageway. Illustratively, the device, or selected portions thereof (e.g., the distal end), can exhibit a degree of flexibility. In this regard, a delivery device, or any portion thereof, may be rigid, malleable, semi-flexible, or flexible. In certain embodiments, an endoluminally advancable device is particularly adapted for moving through and into body passages that angulate sharply or curve abruptly such as when traversing the alimentary canal, passing through and into a fistula opening, traversing a fistula tract, etc. In some of these embodiments, the device is configured to be directable or steerable through the passageway, and therefore, exhibits desirable characteristics, e.g., sufficient stiffness, to allow an operator to apply an adequate degree of ante-grade force to the device to allow it to traverse a passageway in a desirable manner.

Suitable materials for forming delivery devices of the invention can include but are not limited to metallic materials including stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). Additionally or alternatively, the delivery device can include material in the form of yarns, fibers, and/or resins, e.g., monofilament yarns, high tenacity polyester, and the like. A delivery device can also include other plastic, resin, polymer, woven, and fabric surgical materials, other conventional synthetic surgical materials, such as a shape-memory plastic, and/or combinations of such materials. Further, appropriate ceramics can be used, including, without limitation, hydroxyapatite, alumina and pyrolytic carbon.

Referring now to FIG. 3, shown is an apparatus 40 that can be used to plug a passageway or other open space in a patient's body. Apparatus 40 includes a delivery device 41 having a distal end 42. Delivery device 41 also has a lumen 43 communicating with a distal end opening 44. Distal end 42 is configured for placement in a patient's body at or near a passageway or other opening to be plugged, and in this regard, delivery device 41 (including its distal end 42) may exhibit any suitable size and shape for such placement. As well, delivery device 41 may be formed with any suitable material for achieving desirable placement, for example, a material exhibiting a flexibility.

Assembly 20 may be positioned in delivery device lumen 43 as shown in FIG. 3, i.e., with second plug member 22 extending into lumen 26 but not far enough to cause first plug member 21 to expand (or only causing minimal expansion). Such a "pre-expanded" delivery configuration allows a smaller diameter delivery device 40 to be used relative to what might be possible if first plug member was already fully or partially expanded. Apparatus 40 also includes an optional pusher device 45 having a lumen 46 to allow suture 31 to extend therethrough. Pusher 45 is configured for translation through delivery device lumen 43, and is effective to push assembly 20 out of distal end opening 44 or hold assembly 20 in position while the delivery device 41 is removed. Pusher 45 has a large enough diameter so that it does not enter first plug member lumen 26 when pushing first plug member 21 through delivery device lumen 43.

In use, distal end 42 can be placed in a patient's body at or near a passageway or other opening to be plugged. Thereafter, pusher 45 can be manipulated to push first plug member 21 and second plug member 22 from delivery device lumen 43 though distal end opening 44. At this point, first plug member 21 may need to be repositioned within the passageway as necessary, for example, by pushing further with pusher 45 and/or indirectly pulling with suture 31. First plug member 21 may or may not fit snugly within the passageway before second plug member 22 is positioned therein. Once first plug member 21 is in a desirable position, suture 31 is used to pull second plug member 22 into lumen 26, while pusher 45 is placed in contact with the second end 25 of first plug member 21, thus providing a counterforce against first plug member 21 and inhibiting its migration from a desirable position in the passageway. Thereafter, delivery device 40 and pusher 45 are removed from the body passageway as necessary.

These and other apparatuses and methods of the invention are particularly useful in treating gastro-cutaneous, entero-cutaneous, colo-cutaneous and other blind-ending fistulae, wherein a delivery device distal end can be advanced through a fistula tract from a secondary fistula opening in the skin and toward a primary fistula opening at a subcutaneous location in the body. In these instances, it may be necessary or at least helpful to have some way to visualize the delivery device distal end and/or one or more parts of the plugging assembly during delivery. Thus, such apparatus components can incorporate a radiopaque member or other radiopaque element for this purpose, or equipment may otherwise be provided for an apparatus component to be visualized. Suitable visualization devices and techniques will be recognized by those skilled in the art, and therefore, are encompassed by the present invention.

In certain embodiments, a delivery apparatus includes a plugging assembly such as assembly 20 in combination with a delivery catheter. In certain beneficial forms, the catheter is controllably separable longitudinally into two or more pieces for removal, for example, as occurs in Peel-Away® catheters available from Cook Incorporated, Bloomington, Ind., USA. Such an apparatus with a separable catheter is particularly useful in treating fistulae that have a secondary opening in the outer skin surface and a primary opening that is relatively difficult to access other than through the fistula tract, e.g. as occurs in a large percentage of enterocutaneous fistulae. In one form, such a catheter delivery system comprises a suitably sized and configured inner dilator, a Peel-Away® sheath, and a "pusher" device that is translatable through the sheath, wherein all of these can be received over an emplaced guidewire.

Figure 4:
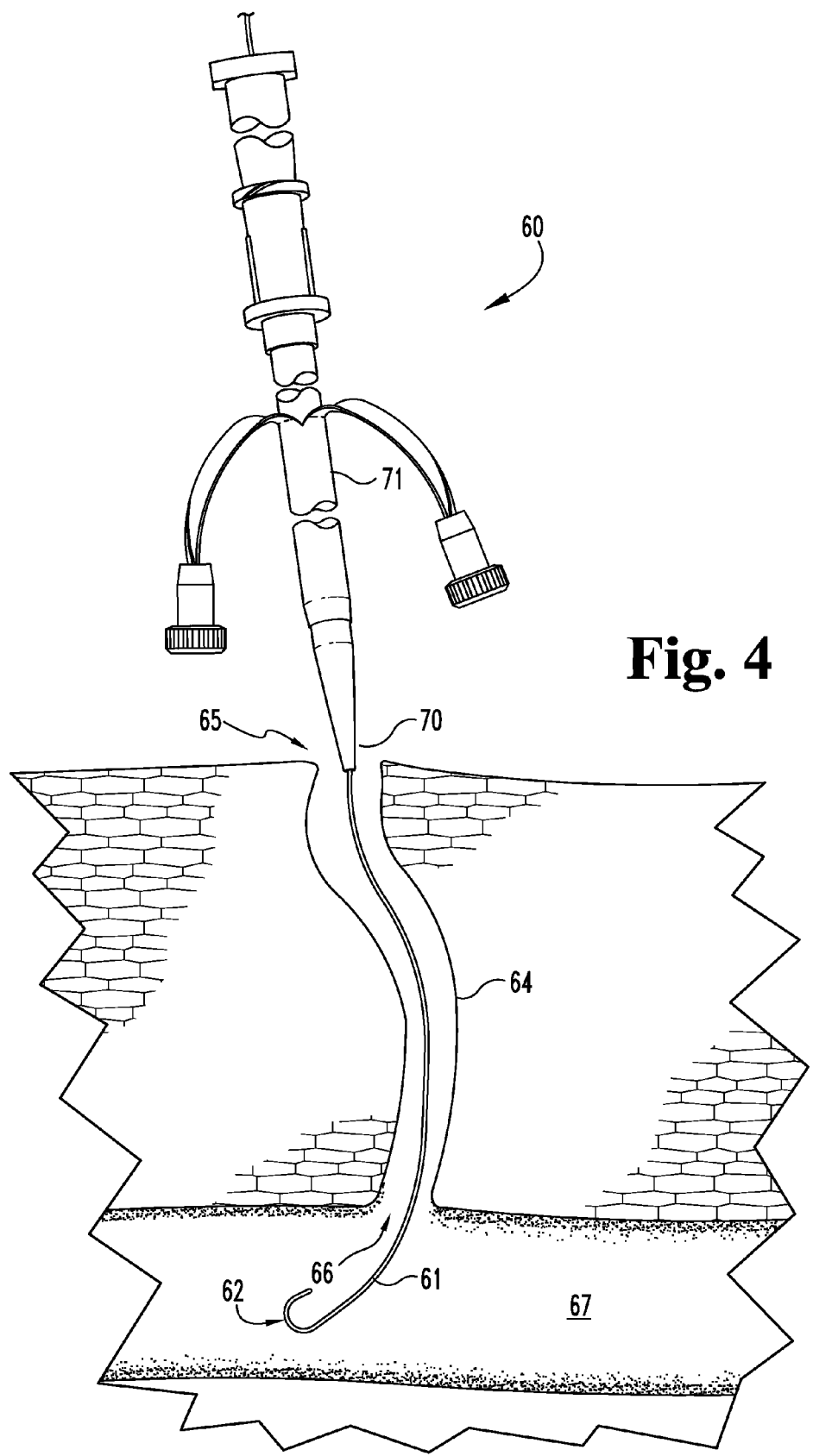
FIG. 4 shows part of an inventive apparatus being used to deliver a plugging assembly to a fistula tract.

FIGS. 4-9 depict an illustrative manner in which an apparatus of this sort can be used to deliver a plugging assembly to a fistula tract. As shown in FIG. 4, a delivery apparatus 60 includes a wire guide 61. The distal end 62 of the wire guide is passed into a fistula tract 64 (e.g., an enterocutaneous fistula tract) through a secondary fistula opening 65 and toward a primary fistula opening 66 under fluoroscopic guidance. The wire is advanced until its distal end 62 enters the alimentary canal 67 through the primary opening. Delivery apparatus further includes a dilator 70 and a sheath 71. The over-the-wire dilator-sheath combination, which is received over wire guide 61, can be advanced through the tract in a similar manner until the distal ends of the two components are positioned at or the primary opening, for example, as depicted in FIG. 5.

Figure 6:
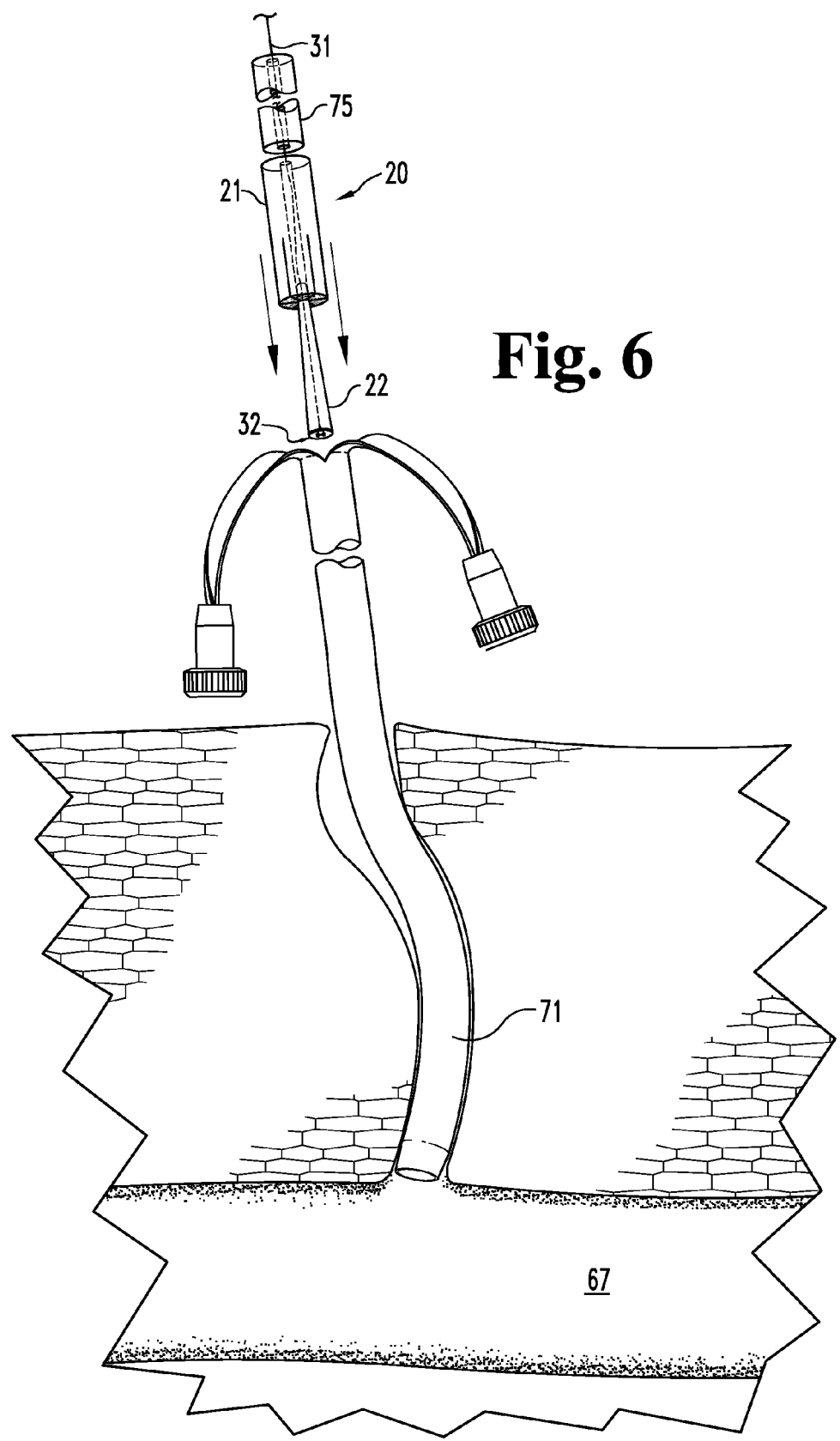
FIG. 6 shows the apparatus of FIG. 4 at a different stage of delivery.
Figure 7:
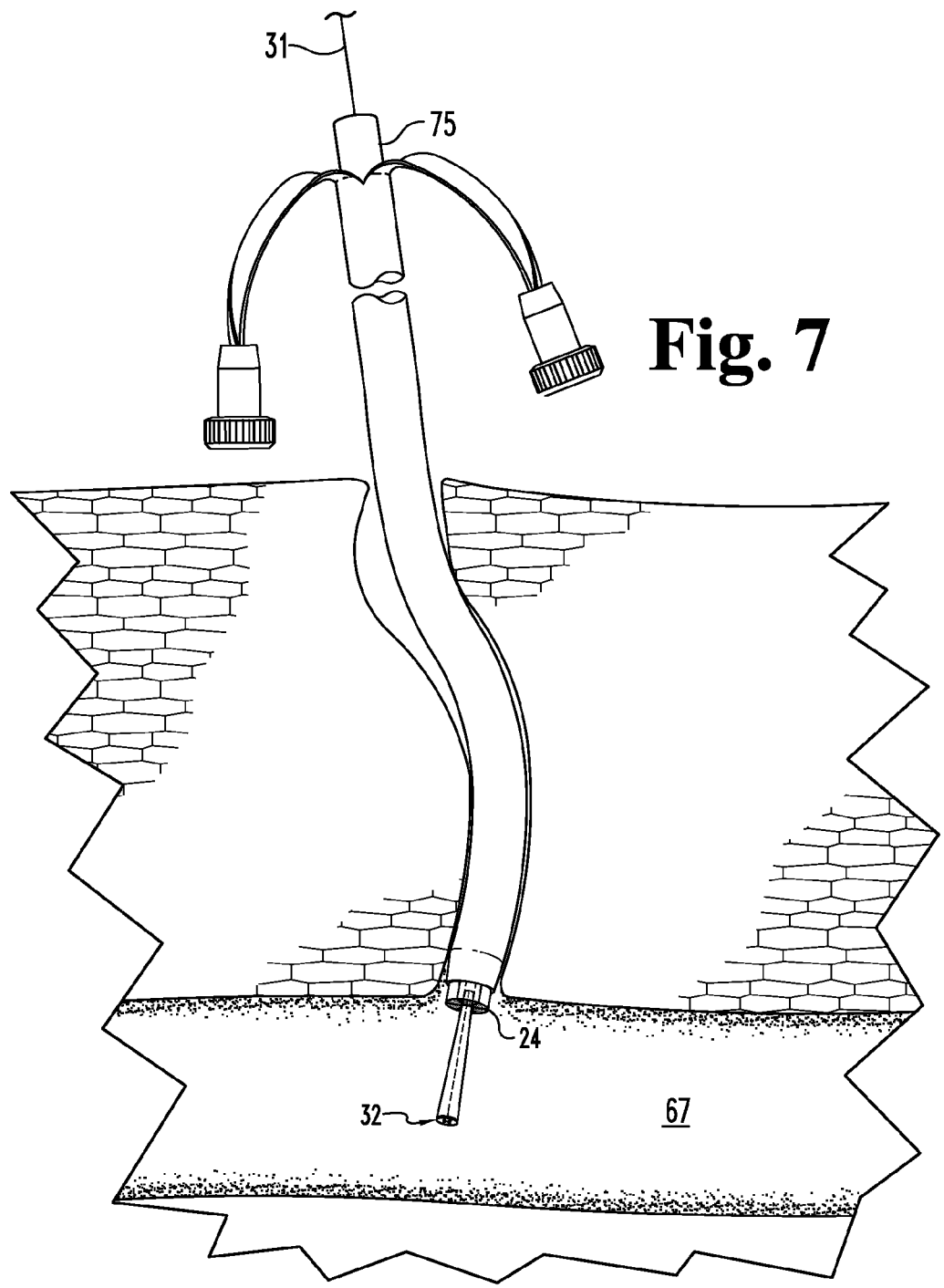
FIG. 7 shows the apparatus of FIG. 4 at a different stage of delivery.

Dilator 70 is then removed, leaving sheath 71 (e.g., a check-flow sheath) in the tract. The wire guide can be removed with the dilator, or alternatively, can be kept in place to assist in subsequent delivery steps. With reference now to FIG. 6, a suitably sized and shaped plugging assembly such as assembly 20 is loaded into the proximal end of sheath 71 in such a way that end cap 32 enters the sheath first, and suture 31 extends from the secondary opening, i.e., remains outside the body. Again, assembly 20 is preferably positioned in the sheath lumen with second plug member 22 extending into the first plug member lumen, but not far enough to cause first plug member 21 to expand (or only causing minimal expansion). An over-the-wire pusher 75 is positioned proximally of assembly 20, and is introduced into the sheath second end (over suture 31). Pusher 75 is advanced toward the sheath first end until at least a portion of assembly 20 is desirably pushed from the sheath distal end, for example, so that first plug member first end 24 is positioned at or near the primary opening, and end cap 32 extends a distance into the alimentary canal as shown in FIG. 7. Again, positioning of the plug members can be aided by fluoroscopic imaging. Additionally, at any point during a delivery procedure and whether or not wholly or partially inside or outside of the delivery sheath, the plug members can be pushed and/or pulled, or otherwise suitably manipulated until they are deemed to be in a desirable position for placement.

Figure 8:
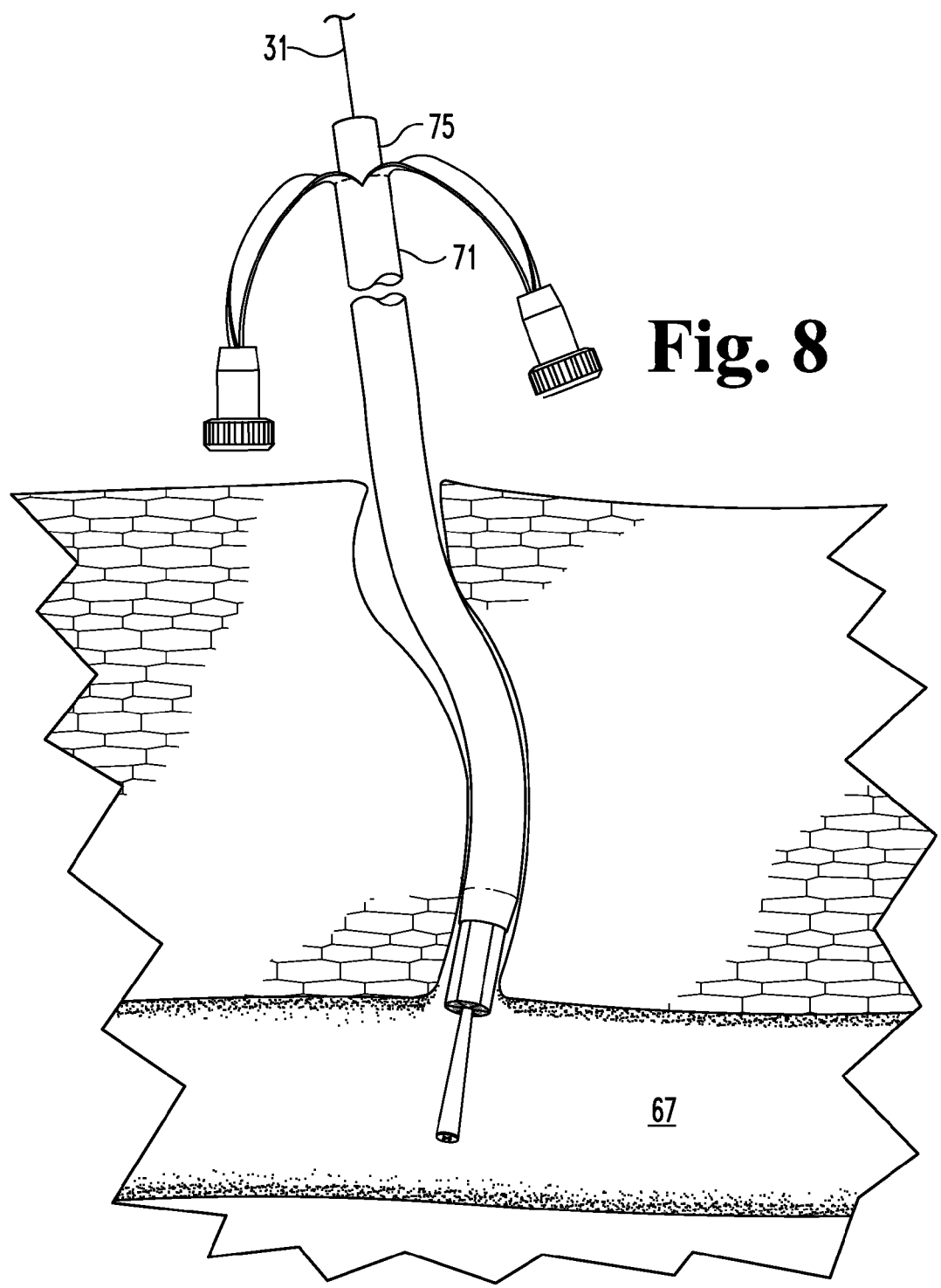
FIG. 8 shows the apparatus of FIG. 4 at a different stage of delivery.
Figure 9:
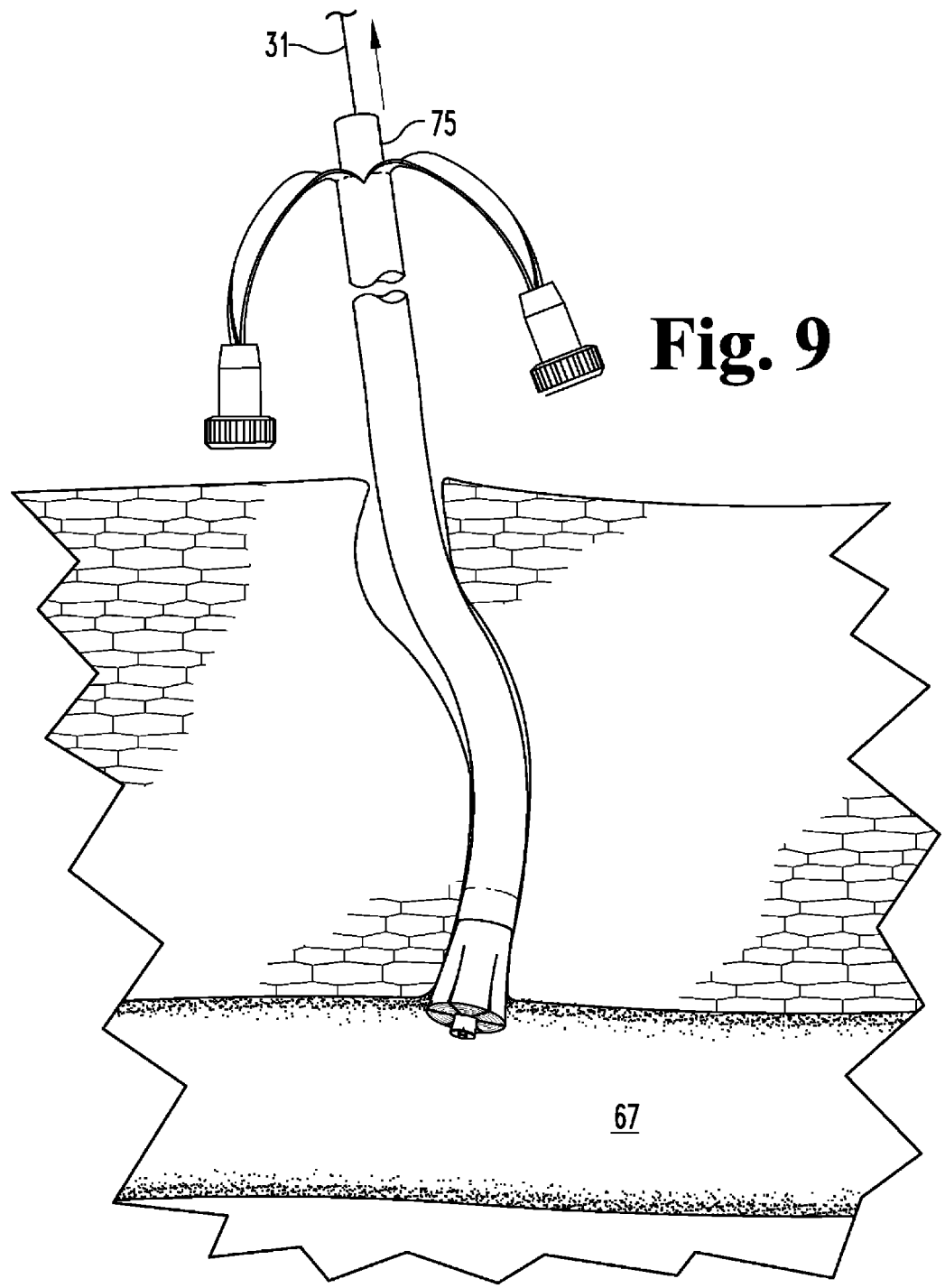
FIG. 9 shows the apparatus of FIG. 4 at a different stage of delivery.

Next, with pusher 75 held in contact with the first plug member second end 25 and providing back pressure, sheath 71 is wholly or partially withdrawn back through the tract, thus maintaining desirable positioning of the plug members in the body. Sheath 71 can be removed entirely from the tract, or alternatively, withdrawn a certain distance in the tract, for example, until it is covering about half of the first plug member as shown in FIG. 8. Referring now to FIG. 9, suture 31 is pulled back through the tract a distance to draw second plug member 22 into first plug member 21, and thereby expand first plug member 21 to plug at least a portion of the fistula tract. If still present, sheath 71 can be removed as the second plug member is being positioned in the first plug member, or alternatively, it can be removed after the second plug member is desirably positioned. Pusher 75 can also be removed, and any desired plug adjustments, manipulations, fixation steps, etc. can be performed. Illustratively, suture 31 can be sutured to skin at or near the secondary opening, e.g., using a free needle, although in some cases, all or a portion of the suture will be removed after the plugging assembly is desirably seated. In placing the assembly, care should be taken to not block or otherwise close the secondary opening to facilitate drainage of the tract following the implantation procedure, for example, during remodeling when a remodelable material is utilized in the plugging assembly.

Suture 31 and other suitable pulling and/or coupling devices may be comprised of one or more of a variety of suitable biocompatible materials exhibiting a rate of degradation upon implantation in vivo, such as but not limited to a 2-0 vicryl suture material. Illustratively, suture 31 can be adapted to desirably hold end cap 32 in association with second plug member first end 29 during product handling and implantation, and then upon implantation, to degrade at a desirable rate. In some modes of operation, an end cap and plug member, at least due in part to degradation of suture 31, can uncouple or otherwise disengage from one another after a period of time following implantation, allowing end cap 32 to be discarded, e.g., to pass through and out of the bowel with naturally occurring fecal mater. In some instances, such decoupling can be facilitated and/or promoted by naturally occurring forces generated during peristalsis.

Contacting and moving a portion of one plug member with another plug member can be accomplished in a variety of manners. In general, such activity will involve some way of bringing about relative motion between the two plug members in the body. In providing a desirable plugging arrangement, one or both of these plug members may be caused or allowed to move. Illustratively, two plug members can each be equipped with one or more pull tethers enabling the plug members to be simultaneously pulled in the body, for example, in generally opposite directions in a bodily passageway. Additionally or alternatively, providing a suitable plugging arrangement can involve directly or indirectly pushing a plug member in the body.

In one embodiment, a first plug member has two sutures extending therefrom, and a second plug member has a single suture extending therefrom. The single suture of the second plug member can be passed through a lumen in the first plug member, wherein the suture(s) of the respective plug members can be grasped and used in placing the second plug member at least partially into the first plug member lumen. In desirably seating the second plug member, the first plug member sutures and/or the second plug member suture can be pulled. Thus, in one illustrative mode of placement, the second plug member suture is held steady to provide an effective counter force as the first plug member sutures are used to pull the first plug member over the second plug member.

Bringing about relative motion between two plug members in the body for plugging purposes will, in some aspects of the invention, involve causing or allowing at least one of the plug members to expand. In some preferred embodiments, a portion of one plug member will be caused or allowed to expand to contact and potentially move a portion of another plug member as part of plugging a body passageway. In this regard, a plug portion having the capacity to expand can include those materials and/or objects that are considered self-expanding, as well as those that require at least some manipulation in order to expand. Illustratively, an inventive plugging assembly can include a first plug member and a second plug member. The first plug member is positionable in a body passageway, and has a cavity or other similar space occurring therein. The second plug member includes a segment positionable in the cavity of the first plug member. The second plug member has a first condition suitable to fit the segment in the first plug member cavity, and a second, expanded condition providing a relatively more snug fit of the segment in the first plug member cavity. In some instances, the second plug member will be effective to contact and move a portion of the first plug member (e.g., in an outward direction) as it changes from the first condition to the second, expanded condition.

Three-dimensionally stable porous matrix materials, such as resilient foam or sponge form materials, can be incorporated into plugging assemblies of the invention. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers. More preferred sponge compositions of the invention will comprise collagen as a matrix-forming material, either alone or in combination with one or more other matrix forming materials. In general, sponge matrices useful in certain embodiments of the present invention can be formed by providing a liquid solution or suspension of a matrix-forming material, and causing the material to form a porous three-dimensionally stable structure; however, a sponge or foam material can be formed using any suitable formation method, as is known in the art.

Illustratively, in the formation of a collageneous sponge or foam material, a collagen solution or suspension can be prepared. The collagen may be derived from mammalian or other animal sources, for example, bovine, porcine or human sources, and desirably is derived from remodelable ECM materials as discussed herein. Synthetically-derived collagen may also be used. The determination of suitable collagen concentrations in the solution will be within the purview of those skilled in the art, with concentration ranges of about 0.05 g/ml to about 0.2 g/ml being typical.

Digestion of the collagen to form the collagen solution is usually carried out under acidic conditions, starting with ground, minced or otherwise comminuted collagen-containing tissue. Optionally, enzymatic digestion may be utilized using known enzymes for this purpose such as pepsin, trypsin, and/or papain. After digestion, the enzymes can be removed by suitable, known techniques.

The collagenous solution and/or suspension can be employed as a moldable or castable material in the formation of the foam or sponge. The cast material can be dried directly without chemical crosslinking or can be crosslinked with a suitable crosslinking agent and then dried. Illustrative crosslinking agents for these purposes include glutaraldehyde, formaldehyde, carbodiimides, UV irradiation, or other crosslinking agents. In preferred embodiments of the invention, the crosslinking agent will contain polar groups that impart a hydrophilic character to the final sponge matrix material. Desirably, a polyepoxide crosslinker is utilized for this purpose, especially a polyglycidyl ether compound. Suitable such compounds include ethylene glycol diglycidyl ether, available under the trade name Denacol EX810 from Nagese Chemical Co., Osaka, Japan, and glycerol polyglycidyl ether available under the trade name Denacol EX313 also from Nagese Chemical Co. Typically, polyglycidyl ethers or other polyepoxide compounds utilized in the invention will have from 2 to about 10 epoxide groups per molecule. The use of such epoxides and/or other crosslinking agents which impart polar groups and a hydrophilic character to the resulting matrix will provide for good wettability and rapid hydration and expansion of certain plugging devices of the invention.

Preferred sources of collagen for forming sponge matrices useful in certain embodiments of the invention include extracellular matrix materials such as submucosa-containing collagenous tissue materials and other collagenous materials as described elsewhere herein. These include, for example, tissue materials comprising small intestinal submucosa, stomach submucosa, urinary bladder submucosa, liver basement membrane, and other basement membrane materials. For additional information as to these collagenous matrix materials and their preparation, reference can be made, for example, to U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety. In forming sponge matrices, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

Sponge matrix materials that can be used to form illustrative devices of the invention can be highly expandable when wetted, so as to achieve an expanded configuration. Illustratively, expandable sponge materials can exhibit the capacity to expand at least 100% by volume, more preferably at least about 200% by volume, and typically in the range of about 300% by volume to about 1000% by volume, when wetted to saturation with deionized water. Sponge materials used in the invention can also exhibit advantageous rates of expansion, achieving volume expansions as noted above in less than about 10 seconds, more preferably less than about 5 seconds, when immersed in deionized water.

Highly compact, dense sponge matrices can be prepared by first hydrating or otherwise wetting a porous sponge matrix, and then compressing and drying the element. Such preparative processes generally provide a more dense, rigid and stably compressed sponge matrix than processes such as simple compaction of the dry sponge matrix. Drying can be conducted sufficiently to stabilize the sponge matrix. For example, preferred drying procedures will reduce the liquid (e.g. water) content of the matrix to less than about 20% by weight, more preferably less than about 10% by weight. Compression forces can be applied so as to achieve a final density and/or desirable configuration, and can be applied in one, two or three dimensions, including radially. The drying of the compacted element can involve lyophilization (or freeze drying) or vacuum drying at ambient or elevated temperatures. When processed in this fashion, upon removal of the compaction force, the sponge matrix is stabilized structurally and remains in its highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

Compressed sponge matrices used in plugging assemblies of the invention can be highly dense, typically having densities of at least about 0.05 g/cm3, preferably in the range of about 0.05 g/cm3 to about 0.2 g/cm3, and more preferably about 0.075 g/cm3 to about 0.2 g/cm3. The compacted sponge matrix can have sufficient rigidity to be deployed by passage through needles, catheters or sheaths, for example by utilizing a push rod or other pusher element to force the sponge matrix graft body through the needle and/or catheter cannula. Expanded sponge densities (dry) will generally be less than the corresponding compacted densities. Typical expanded densities (dry) will range from about 0.01 g/cm3 to about 0.1 g/cm3, more preferably about 0.02 g/cm3 to about 0.07 g/cm3.

Compressed sponge materials may also contain agents which promote further retention of the compressed, high density form of the matrices. These may include for example starch, cellulose, sugars such as dextrose, or glycerin. Such agents can optionally be included in the liquid (preferably aqueous) used to hydrate or otherwise wet the sponge prior to compaction and drying. For additional information concerning foam or sponge form materials that can be useful in certain embodiments of the present invention, reference can be made, for example, to U.S. Pat. App. Pub. No. 2003/0013989.

In additional embodiments, plug members useful in the invention can include ECM materials and other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a plugging device. Illustratively, the expanded material can be enriched with bioactive components, dried, and/or molded, etc., in the formation of a desirably shaped and configured plug construct. In certain embodiments, a dried plug member formed with the expanded ECM material can be highly compressible (or expandable) such that the material can be compressed for delivery, such as from within the lumen of a cannulated delivery device, and thereafter expand upon deployment from the device so as to become anchored within a particular space (e.g., within a passageway or other similar space in the body, in a lumen or cavity of another plug, etc.) and/or cause closure of the space.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of sponge or foam shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a plugging assembly component.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression.

Expanded collagenous materials can be used in preparing a wide variety of plugging devices. Methods for preparing such plugging devices can include contacting an ECM or other collagenous starting material with an alkaline substance in an amount effective to expand the material, casting or otherwise forming the expanded collagenous material into a plug member shape (e.g. one of those described herein), and lyophilizing the expanded material to form a dried plug member.

Compact, stabilized sponge materials and other expandable materials, when used in the invention, can allow a plug member to attain a more low-profile condition during a deployment step. For example, an illustrative plugging assembly can include a first plug member and a second plug member. The first plug member has a lumen or other similar open space therein. The second plug member is comprised of an expandable material such that in a stabilized, compressed first condition, the plug member can fit within an end of a delivery device (e.g., a probing device, catheter, delivery sheath, or other similar instrument), which is sized and configured to at least partially enter the lumen of the first plug member. Thereafter, the second plug member can be pushed or otherwise removed from the delivery device in a suitable manner to allow the second plug member to attain an expanded second condition. In such an expanded condition, the second plug member, which was previously able to easily pass into the first plug member lumen, is now somewhat lodged or at least relatively more lodged within the lumen.

Figure 10:
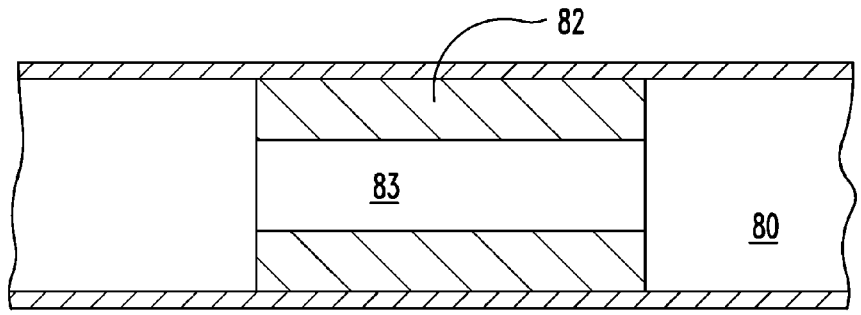
FIG. 10 shows one step in delivering an inventive assembly to a body passageway for plugging the passageway.
Figure 11:
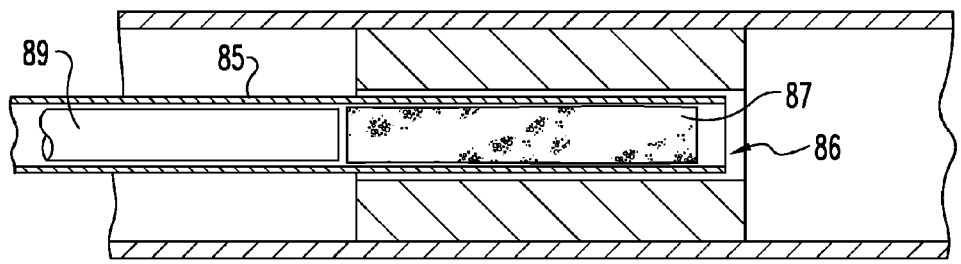
FIG. 11 shows another step in delivering an inventive assembly to a body passageway for plugging the passageway.

FIGS. 10-13 show an illustrative manner in which another plugging assembly of the invention can be delivered to a body passageway 80. A first plug member 82 having a central lumen 83 can be delivered to a location in the passageway as shown in FIG. 10. Such a plug member can exhibit a variety of shapes and sizes, and in some cases, will by itself fit snugly in the body passageway. Thereafter a delivery device 85 having a lumen communicating with a distal end opening 86 is advanced a distance into the first plug member lumen, for example, as shown in FIG. 11. Residing within the delivery device lumen and positioned at or near its distal end opening 86 is an expandable, second plug member 87. This plug member can be formed with one or more of a variety of materials. In a preferred embodiment, second plug member 87 includes a collagen-containing material having the capacity to expand. A pusher 89 is positioned proximal of the second plug member in the delivery device lumen, and can translate in the lumen. Thus, efforts to expel the second plug member from the lumen can involve holding the delivery device steady while advancing the pusher, holding the pusher steady while withdrawing the delivery device, or both.

Figure 12:
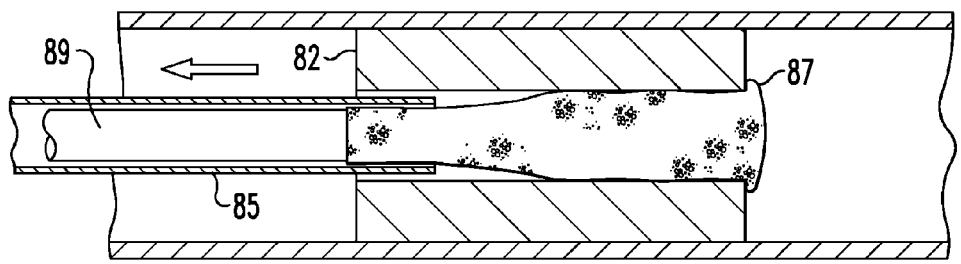
FIG. 12 shows another step in delivering an inventive assembly to a body passageway for plugging the passageway.
Figure 13:
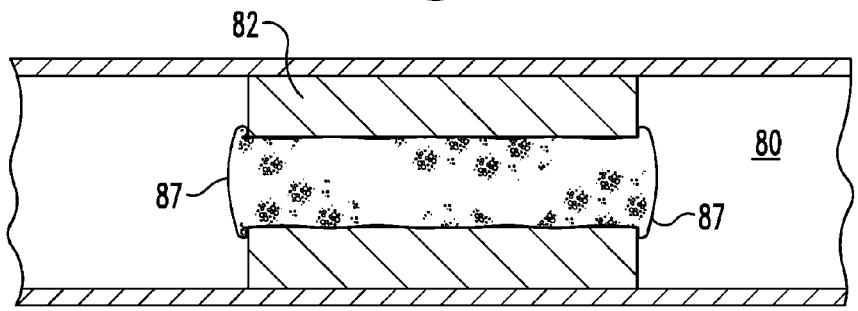
FIG. 13 shows another step in delivering an inventive assembly to a body passageway for plugging the passageway.

FIG. 12 shows second plug member 87 as it is being expelled from the delivery device lumen and at least partially into the first plug member lumen. In this specific illustrative embodiment, such expulsion is accomplished by holding pusher 89 generally in place and in contact with the proximal end of the second plug member, while withdrawing the delivery device in the direction of the arrow shown. As second plug member 87 exits the delivery device lumen, it expands to fill at least a portion of the first plug member lumen. FIG. 13 shows the plugging assembly after second plug member 87 has been completely removed from the delivery device lumen, and the delivery device and pusher have been withdrawn from the body. While not necessary to broader aspects of the invention, in some embodiments, an expanded plug member such as that shown in FIG. 13 will exert a certain amount of force on walls of a plug member lumen in which it is positioned. In this regard, a plug member such as plug member 87 can be configured to exert varying amounts of force on a plug lumen wall as it expands. Also, when such a force is exerted, it may or may not be effective to outwardly displace a portion of the plug member to which it is applied.

Expansion of one plug member such as plug member 87 in a lumen or other open space in another plug member may be sufficient to obviate the need for otherwise securing the two plug members together, although additional steps to secure the plug members (e.g., suturing, bonding, etc.) may be taken. In some modes of operation, an adhesive will be placed on one or both of the plug members prior to expansion of the second plug member. Additionally, in certain aspects, a second plug member will include portions residing externally of the first plug member lumen upon expansion of the second plug member in this lumen. In some embodiments such as that shown in FIG. 13, these portions, upon expanding, will have a diameter that is greater than that of the first plug member lumen. Such external, expanded portions can provide enhanced closure of the first plug member lumen by the second plug member.

In certain aspects of the invention, treatment of a fistula includes an endoscopic visualization (fistuloscopy) step that is performed prior to implanting a fistula plug. Such endoscopic visualization can be used, for example, to determine the shape and size of a fistula, which in turn can be used to select an appropriately sized and shaped fistula graft device for treating the fistula. Illustratively, a very thin flexible endoscope can be inserted into a secondary opening of the fistula and advanced under direct vision through the fistula tract and out through the primary opening. By performing fistuloscopy of the fistula, the primary opening can be accurately identified. Also, certain fistula treatment methods of the invention include a fistula cleaning step that is performed prior to implanting a fistula graft. For example, an irrigating fluid can be used to remove any inflammatory or necrotic tissue located within the fistula prior to engrafting the graft device. In certain embodiments, one or more antibiotics are applied to the fistula graft device and/or the soft tissues surrounding the fistula as an extra precaution or means of treating any residual infection within the fistula.

Additionally, an inventive device, or any component thereof, can incorporate an effective amount of one or more antimicrobial agents and/or therapeutic agents otherwise useful to inhibit the population of the device and surrounding tissue with bacteria and/or other deleterious microorganisms. Illustratively, a device can be coated with one or more antibiotics such as penicillin, tetracycline, chloramphenicol, minocycline, doxycycline, vancomycin, bacitracin, kanamycin, neomycin, gentamycin, erythromycin and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone, and antiseptics (substances that prevent or arrest the growth or action of microorganisms, generally in a nonspecific fashion) such as silver sulfadiazine, chlorhexidine, glutaraldehyde, peracetic acid, sodium hypochlorite, phenols, phenolic compounds, iodophor compounds, quaternary ammonium compounds, and chlorine compounds. These or other therapeutic agents can be incorporated directly on or in an inventive device, or they can be incorporated with a suitable binder or carrier material, including for instance hydrogel materials. The carrier or binder coating can be applied to the device by any suitable means including, for example, spraying, dipping, etc. as known in the art. The antimicrobial or other therapeutic agent can be added to the carrier/binder coating either prior to or after application of the coating to the device.

Further, the delivery systems and methods of the present invention can be adapted for delivering plugging assemblies into one or multiple fistula tracts in a given medical procedure. In this context, the term "fistula tract" is meant to include, but is not limited to, a void in soft tissues extending from a primary fistula opening, whether blind-ending or leading to one or more secondary fistula openings, for example, to include what are generally described as simple and complex fistulae. In cases of complex fistulae, for example a horseshoe fistula, there may be one primary opening and two or more fistula tracts extending from that opening. In such instances, a fistula graft may be delivered to any of the fistula tracts.

In some modes of operation, means for visualizing and/or irrigating a fistula can be received within a delivery device lumen. Illustratively, such means, as well as other desirable instruments and/or materials, can be passed into the proximal end of a delivery device lumen (or alternatively, can be passed into one or more openings in a sidewall of the delivery device), and through at least a portion of the delivery device lumen. For example, in certain aspects, a delivery device includes one or more ports in a sidewall thereof, wherein each port can be associated with a corresponding channel that extends from the port toward the distal end of the delivery device. In some forms, one or more port and channel combinations are each configured to receive one or more instruments and/or materials therethrough. For example, a port can be configured to receive one or more optical fibers for visualization and/or illumination of the fistula and surrounding soft tissues, for example, fiber-optic bundles including a plurality of glass fibers comprised of silicone, silicone dioxide, and/or a suitable equivalent. When used in the invention, these optical fibers are provided having suitable characteristics for the particular application including but not limited to suitable lengths and diameters, as well as degrees of flexibility or malleability. Suitable delivery device ports can also be configured to receive fluids for the ante-grade irrigation of a fistula. Such fluids can be provided from an external bag of fluid that is connected to the port of the irrigation channel by means of flexible tubing. If necessary, the fluid can be infused under pressure using a pressure bag applied to the fluid source, to increase the pressure under which the fluid is infused. Suitable delivery device ports can further be configured to receive guide-wires, drains, solutions such as sealants or sclerosants, high intensity light sources, a lever system to steer the delivery device (e.g., wherein the delivery device and/or its distal tip is directable in one, two, or three planes), and/or any other suitable instruments and/or materials. In some forms, a delivery device port is configured to receive an optical viewing and lens system that may be attached to a video camera, a video monitor, and a video recorder for viewing at the distal end of the delivery device.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A device for plugging a passageway in the body, comprising:
   a first plug member comprised of a porous matrix material configured to promote cellular invasion and ingrowth into said first plug member, said first plug member having a proximal segment and a distal segment;
   a removable second plug member comprised of a porous matrix material positioned in the first plug member, wherein said second plug member comprises a rolled sheet-form material that includes a tapered longitudinal segment, the second plug member effective to force at least said distal segment of the first plug member to radially expand to a radially expanded state and fill at least a segment of the passageway as the second plug member is being positioned in the first plug member, and wherein said proximal segment is configured to extend within the passageway proximally of said distal segment with said distal segment in said radially expanded state;
   a pulling member extending from said second plug member, said pulling member configured to exert a pull force on said second plug member; and
   a pushing member configured to provide a counterforce against said first plug member during exertion of said force.

2. The device of claim 1, wherein the first plug member has a lumen extending therethrough, and wherein the second plug member is positioned in said lumen.

3. The device of claim 2, wherein the lumen includes a tapered portion.

4. The device of claim 2, wherein the second plug member includes a longitudinal segment lodged in a portion of said lumen, and wherein the circumference of said longitudinal segment is greater than the circumference of said lumen portion prior to said longitudinal segment being lodged in said lumen portion.

5. The device of claim 2, wherein said lumen includes an opening to the exterior of the first plug member, and wherein said second plug member includes a longitudinal segment that extends through said opening and is lodged in said opening, and wherein the diameter of said longitudinal segment is greater than the diameter of said opening prior to said longitudinal segment being lodged in said opening.

6. The device of claim 2, wherein said lumen has a generally constant diameter along its length.

7. The device of claim 2, wherein:
   said pulling member extends through said lumen in said first plug member; and
   said pushing member has a lumen extending therethrough configured to allow said pulling member to extend therethrough.

8. The device of claim 1, wherein the first plug member comprises a generally conical portion.

9. The device of claim 1, wherein the first plug member includes a plurality of movable wedge portions effective to enhance expansion of the first plug member in the body passageway.

10. The device of claim 1, wherein the second plug member comprises a generally conical portion.

11. The device of claim 1, wherein the second plug member is comprised of a naturally-derived biocompatible material.

12. The device of claim 1, wherein:
    the first and second plug members are translatable longitudinally relative to one another while in frictional engagement with one another; and
    the second plug member is constructed and arranged to force at least a segment of the first plug member to radially expand when at least a portion of the second plug member is translated longitudinally from a position external of the first plug member to a position internal of the first plug member.

13. The device of claim 1, wherein:
    said device is carried within a delivery apparatus, said apparatus comprising a cannulated device configured to be controllably separable longitudinally into two or more pieces.

14. An assembly for plugging a passageway in the body, comprising:
    a first plug member having a first plug member lumen, said first plug member comprised of a porous matrix material configured to promote cellular invasion and ingrowth;
    a second plug member comprised of a porous matrix material configured to promote cellular invasion and ingrowth positionable in said first plug member lumen and effective as it is being positioned in said first plug member lumen to cause at least part of the first plug member to become outwardly displaced for plugging the body passageway with the first plug member having the second plug member positioned in said first plug member lumen;
    a pulling member extending from the second plug member and receivable through said lumen, the pulling member configured to exert a pull force on said second plug member sufficient to translate the second plug member in said lumen of said first plug member so as to cause at least part of the first plug member to become outwardly displaced for plugging the body passageway, and wherein said pulling member comprises a flexible tether; and
    a pushing member selectively receivable against and removable from contact with said first plug member and operable to provide a push force on the first plug member during exertion of said pull force, said push force directed generally opposite said pull force.

15. The assembly of claim 14, wherein said first plug member lumen has a generally constant diameter along its length.

16. The assembly of claim 15, wherein the second plug member has a varying diameter along it length.

17. The assembly of claim 14, wherein the second plug member includes an expandable portion.

18. The device of claim 14, further comprising a delivery device having a lumen communicating with a distal end opening, the delivery device configured for passage through a body passageway, wherein the first plug member and the second plug member are received in the delivery device lumen, wherein said pushing member is receivable in said delivery device lumen, said pushing member having a pushing member lumen extending through said pushing member, and wherein said flexible tether extends through said pushing member lumen.

19. The assembly of claim 18 wherein:
    said delivery device is configured to be controllably separable longitudinally into two or more pieces.

20. The apparatus of claim 14, wherein:
at least a portion of the second plug member is translatable longitudinally into the first plug member lumen while frictionally engaging a wall defining the first plug member lumen; and
the second plug member is constructed and arranged to cause at least part of the first plug member to become outwardly displaced when said at least a portion of the second plug member is translated longitudinally from a position external of the lumen of the first plug member to a position within the lumen of the first plug member.

21. An assembly for plugging a passageway in the body, comprising:
a first plug member comprised of a porous matrix material configured to promote cellular invasion and ingrowth into said first plug member, said first plug member having a cavity therein and positionable in a body passageway, wherein said cavity is a lumen extending completely through the first plug member from a first opening to a second opening said first plug member constructed and arranged to be deployed within the passageway so as to by itself maintain a snug fit extending circumferentially around and against the passageway; and
a second plug member comprised of a porous, collagen-containing matrix material, said second plug member having a first end portion and a second end portion, said second plug member including a segment positionable in the cavity of the first plug member, wherein said segment is of sufficient length to completely fill said lumen, the second plug member having a first condition suitable to deliver the segment to the first plug member cavity, and a second, expanded condition providing a more snug fit of the segment in the first plug member cavity relative to the first condition of the second plug member, wherein said assembly is configured to extend through the passageway and plug at least a segment of the passageway, wherein when said segment of said second plug member is deployed in said lumen, said first end portion resides external of said lumen and adjacent said first opening and expands to a diameter greater than a diameter of said first opening, and said second end portion resides external of said first plug member adjacent said second opening and expands to a diameter greater than said second opening.

22. The assembly of claim 21, wherein said cavity is a lumen extending through at least a segment of the first plug member.

23. The assembly of claim 22, wherein the diameter of said lumen varies along the length of said lumen.

24. The assembly of claim 22, wherein said lumen extends entirely through the first plug member.

25. The assembly of claim 24, wherein said segment is of sufficient length to extend at least the length of said lumen.

26. The assembly of claim 21, wherein:
said assembly further comprises a pulling member extending through said cavity in said first plug member; and
a pushing member having a lumen extending therethrough configured to allow said pulling member to extend therethrough.

27. The assembly of claim 21
said assembly is carried within a delivery apparatus, said apparatus comprising a cannulated device configured to be controllably separable longitudinally into two or more pieces.

* * * * *